United States Patent [19]
Nichols

[11] 4,336,795
[45] Jun. 29, 1982

[54] DEROTATION BRACE

[76] Inventor: Steven B. Nichols, 739 Wildwood Rd., West Hempstead, N.Y. 11552

[21] Appl. No.: 257,862

[22] Filed: Apr. 27, 1981

Related U.S. Application Data

[62] Division of Ser. No. 13,470, Feb. 21, 1979, Pat. No. 4,263,901.

[51] Int. Cl.³ .............................................. A61F 3/00
[52] U.S. Cl. ................................................ 128/80 A
[58] Field of Search ................... 128/80 A, 80 R, 83, 128/87 R, 87 C, 82, 69

[56] References Cited

U.S. PATENT DOCUMENTS

| | | | |
|---|---|---|---|
| 828,221 | 8/1906 | Langel | 128/69 |
| 1,077,119 | 10/1913 | Bixby | 151/15 |
| 2,514,870 | 7/1950 | Isreal | 128/80 A |
| 2,585,342 | 2/1952 | Murlan | 128/80 J |
| 2,630,801 | 3/1953 | Fiest et al. | 128/80 A |
| 2,774,151 | 12/1956 | Dahlquist et al. | 36/59 R |
| 2,804,070 | 8/1957 | Faulkner | 128/80 A |
| 2,815,021 | 12/1957 | Freeman | 128/80 A |
| 2,822,623 | 2/1958 | Legois | 33/189 |
| 2,834,116 | 5/1958 | Hambrick | 33/189 |
| 2,906,261 | 9/1959 | Craig | 128/80 A |
| 2,920,620 | 1/1960 | Rogers | 128/80 A |
| 2,950,715 | 8/1960 | Brobeck | 128/71 |
| 2,963,020 | 12/1960 | Moran | 128/80 A |
| 3,265,003 | 8/1966 | Friedman | 128/80 A |
| 4,088,129 | 5/1978 | DiGiulio | 128/80 A |

FOREIGN PATENT DOCUMENTS 456621 2/1975 U.S.S.R. .............................. 128/80 J

OTHER PUBLICATIONS

"Ortho", Orthopedic Appliances Atlas, 1952, pp. 485-493.
*Callender D-Rotation Brace*, De Puy Ad Brochure, P.O. Box 988, Warsaw, Ind. 46580.
*Unibar*, Spectra Industries Ad Brochure, 405 Baily Rd., Yeadon, Pa. 19050.

*Primary Examiner*—John D. Yasko
*Attorney, Agent, or Firm*—Frishauf, Holtz, Goodman and Woodward

[57] ABSTRACT

An orthopedic appliance comprises a pair of bar-like members pivotally connected together in the vicinity of respective ends thereof, and plate-like members adjustably connected to respective free ends of the bar-like members for connection to the shoes of a patient. A scale is provided at the pivotal interconnection of the bar-like members to indicate the relative orientations of the bar-like members. A locking device is provided to lock the bars at their desired relative positions.

7 Claims, 7 Drawing Figures

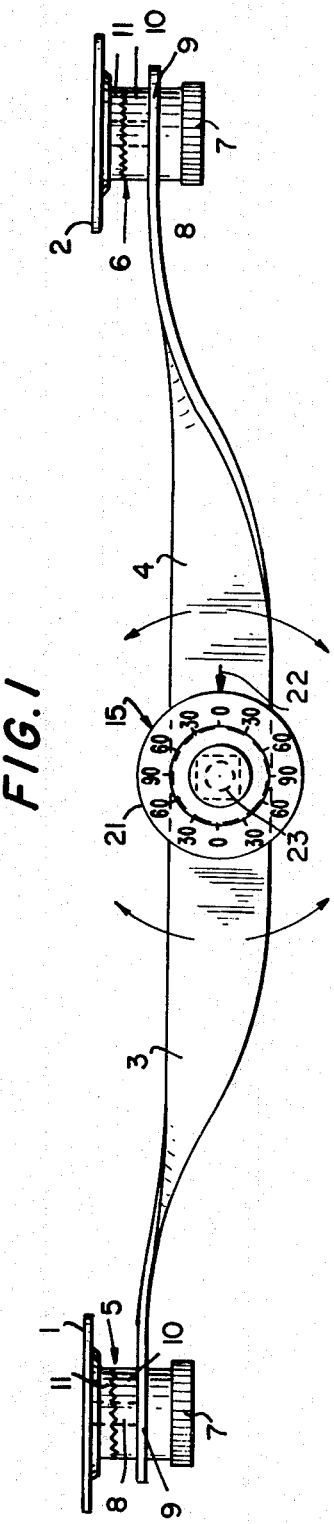
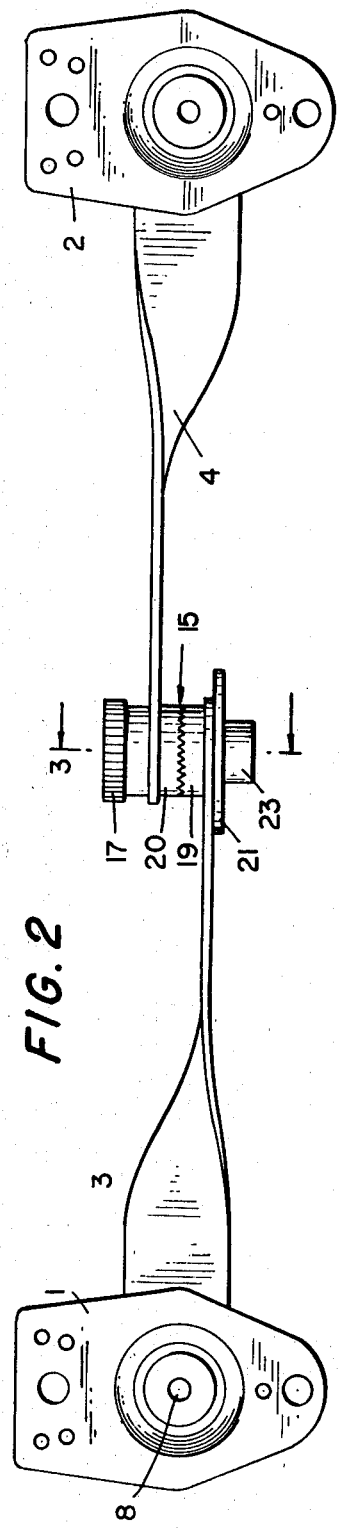
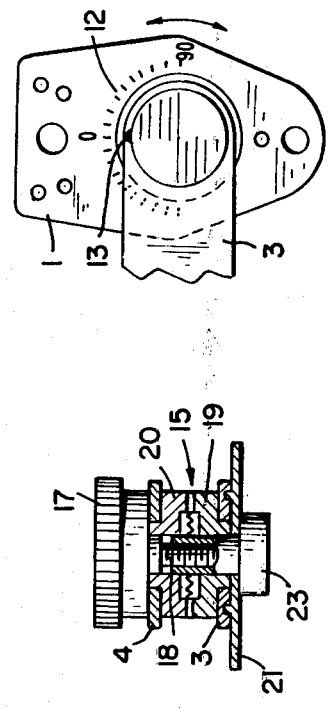

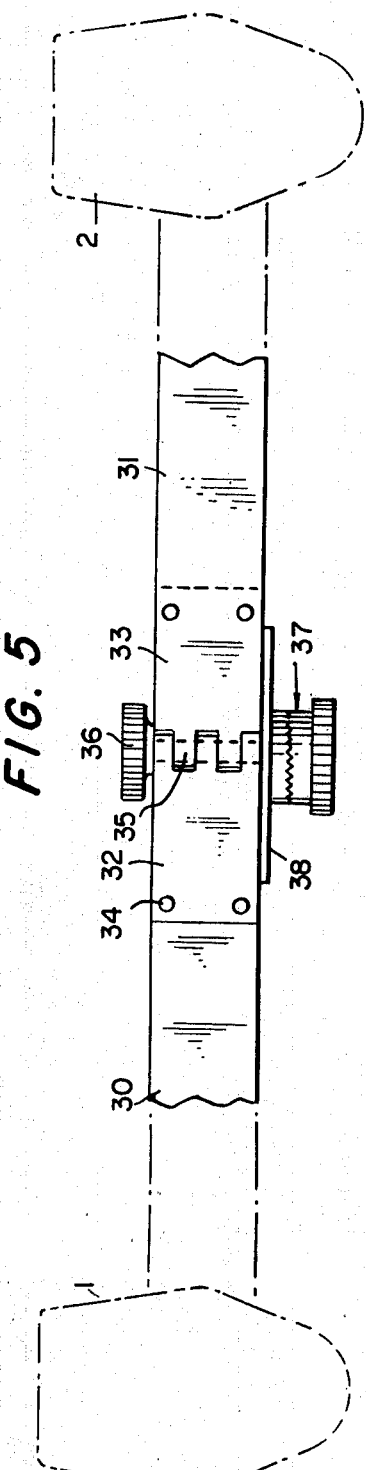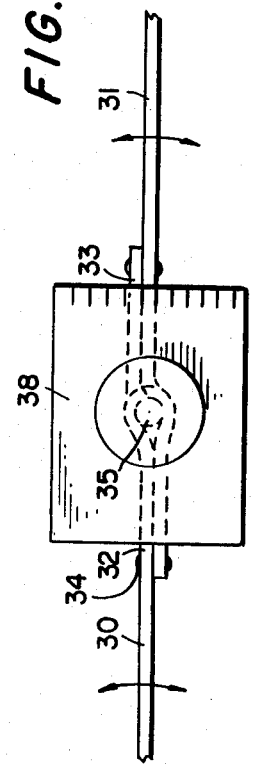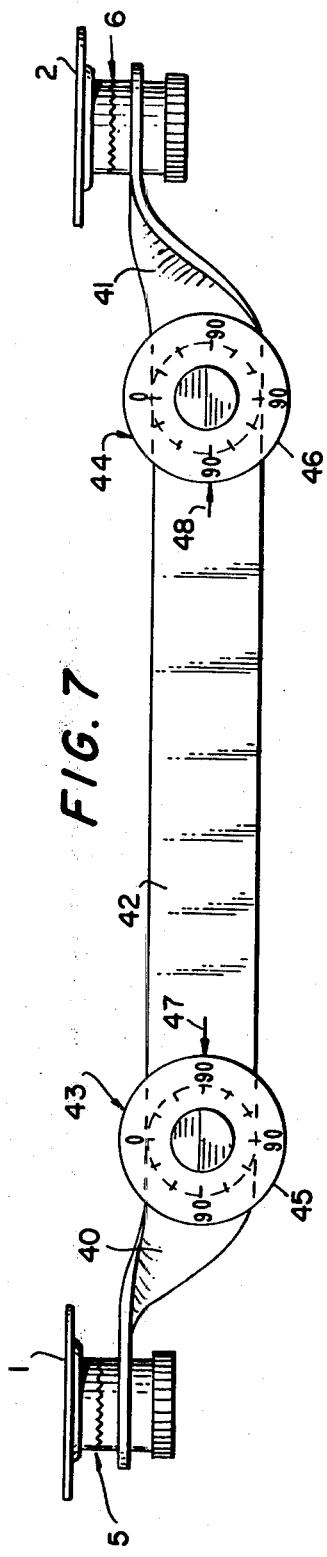

DEROTATION BRACE

This is a division of application Ser. No. 13,470 filed Feb. 21, 1979, which issued as U.S. Pat. No. 4,263,901 on Apr. 28, 1981.

BACKGROUND OF THE INVENTION

This invention relates to orthopedic devices, and more particularly to corrective orthopedic devices for treating deformities in children's legs or feet.

Numerous orthopedic devices for correcting deformities in children's legs or feet are known. The object of the present invention is to provide a simplified orthopedic device which provides all of the desired degrees of correction, but yet which is simple in construction, easy and economical to manufacture and easy for the operator to accurately adjust to provide precise orthopedic correction.

SUMMARY OF THE INVENTION

In accordance with the present invention, an orthopedic appliance comprises at least two elongated members pivotally connected together; means adjustably connected to respective free ends of the elongated members for connection to a shoe of a patient; means at the pivotal connection of the elongated members for releasing and locking the pivotal connection to permit pivoting of the elongated members relative to each other and locking of the elongated members relative to each other when a desired relative angular orientation is reached; and scale means at the pivotal connection for indicating the angular orientation of the elongated members relative to each other. Preferably, the means for adjustably connecting the ends of the elongated members to a shoe of a patient also includes scale means to indicate relative angular orientation thereof.

BRIEF DESCRIPTION OF THE DRAWINGS

FIG. 1 is a side view of a first embodiment of the invention;

FIG. 2 is a top view of the embodiment of FIG. 1;

FIG. 3 is a sectional view taken along the line 3—3 in FIG. 2;

FIG. 4 is a bottom view of the shoe connecting member in the embodiment of FIGS. 1 and 2;

FIG. 5 is a top view of another embodiment of the invention;

FIG. 6 is a side view of the central hinge portion in the embodiment of FIG. 5; and FIG. 7 is a side view of yet another embodiment of the invention.

DETAILED DESCRIPTION

Referring to FIGS. 1-4, the orthopedic device of the present invention comprises two plate-like members 1,2 for attachment to the soles of shoes of the wearer by means of rivet, screws or other suitable attaching means passing through holes in the plate-like members 1,2. The plate-like members 1,2 are adjustably connected to respective bar members 3,4 via adjustable coupling members 5,6. The adjustable coupling members 5 and 6 are identical and the constituent elements of only coupling member 5 are described. Coupling member 5 comprises a knurled member 7 having a threaded shaft or screw 8 connected thereto and extending through a hole or aperture 9 in bar member 3. A washer-like member 10 with a serrated upper surface is preferably fixedly attached to bar member 3. A mating washer-like member 11 with a complementary serrated lower surface is preferably fixedly attached to plate-like member 1. The threaded shaft 8 is threadably received in the upper washer-like member 11. In use, the knurled knob 7 is loosened and the plate-like member 1 is rotated about the longitudinal axis of shaft 8 to the desired position. The knurled knob 7 is then tightened, locking the serrations of members 10 and 11 together to fixedly retain the plate 1 in the desired position. Any other type of suitable coupling and adjusting means may be used in place of coupling members 5,6. Also, a shoe may be adhesively bonded to plates 1,2 instead of being screwed or riveted thereto.

The under surfaces of plate-like members 1,2 have a scale 12 thereon for indicating the degree of rotation of the plate-like members about the threaded shaft 8. A marker 13 is formed on the bar-like members 3,4 to which the plate-like members 1,2 are respectively attached to indicate the angle on the scale. See FIG. 4.

The bar-like members 3,4 are adjustably connected together by means of a further coupling member 15. The bar-like members 3,4 are bent about the longitudinal axes thereof so that the flat surfaces thereof in the vicinity of the coupling 15 lie in a vertical plane (as seen in the view of FIG. 1), whereas the remote free ends in the vicinity of coupling members 5,6 lie in a horizontal plane.

The coupling member 15 is shown in detail in FIG. 3. A knurled knob 17 has a threaded screw-like member 18 extending therefrom, the screw passing through serrated members 19,20, the serrations of which face each other. Preferably, the serrated members 19,20 are fixedly and non-rotationally connected to their respective bar-like members 3,4. A scale member 21, preferably in the form of a washer, having scale indications thereon is fixedly attached to the bottom of bar-like member 3 (see also FIG. 1). The bottom of bar-like member 4 has a mark 22 thereon (see FIG. 1) which cooperates with the scale on scale member 21. A female threaded nut member 23 passes through the bottom bar-like member 3 and threadably engages the threaded screw 18.

In use, the knurled member 17 is turned counterclockwise to loosen the connection between screw 18 and female threaded member 23. Then, the bar-like members 3,4 are adjusted in the direction of the arrows shown in FIG. 1 to the desired relative angular orientation, the angular orientation being indicated by marker 22 cooperating with the scale member 21. When the desired angular orientation is achieved, the knurled member 17 is turned clockwise to tighten the connection. By tightening the connection, the serrations of serrated members 19 and 20 engage each other so as to more securely lock the bar members 3,4 relative to each other.

Any other type of suitable coupling means may be used in place of the coupling means 15, providing that the coupling means has the proper characteristics to provide a secure, positive engagement between the bar-like members. The bar-like members 3,4 are shown as flat members which are bent around the longitudinal axes thereof. Other suitable members, such as round members, could be used, with the appropriate interconnections at the ends thereof and with the appropriate interconnection to the plate-like members 1,2. For example, round bar stock with flattened ends would be suitable, or round bar stock with flat engaging members welded or otherwise secured to the ends thereof would also be suitable.

FIG. 5 illustrates a modified embodiment of the invention which comprises plate-like members 1, 2 which are substantially the same as those illustrated in FIGS. 1-4, adjustably mounted to the ends of elongated members 30, 31, respectively. The plate-like members 1, 2 are interconnected with elongated members 30, 31 via respective adjustable couplings, such as couplings 5, 6 of FIGS. 1-4 and have suitable scales associated therewith, for example as illustrated in FIG. 4. The elongated members 30, 31 have respective hinge members 32, 33 at the opposite ends thereof. As shown in FIGS. 5 and 6, the hinge members 32, 33 are integral with the elongated members 30, 31, respectively, and are formed by bent over ends of the respective elongated members 30, 31. The ends have mating slots and projections, as seen in FIG. 5, with a hinge pin 35 extending therethrough about which the hinge members 32, 33 pivot. Hinge pin 35 has a knurled knob 36 at one end thereof and an adjustable serrated coupling device 37 at the other end thereof, the coupling device 37 being substantially similar to the coupling devices 5 and 6 illustrated in FIG. 1. The operation of coupling member 37 is the same as coupling members 5 and 6 illustrated in FIG. 1 and are not further described.

One of the elongated members (30) has a scale plate 38 secured thereto, for example by welding or other suitable means. The scale plate 38 has scale markings on the right hand edge thereof as seen in FIG. 6 which cooperate with the elongated member 31 to indicate the relative angle between elongated members 30 and 31. In operation, the knurled knob 36 is turned counterclockwise to loosen the adjustable connection 37, the bars or elongated members 30, 31 are adjusted to the desired angular orientation, and the knurled knob 36 is then tightened to secure the connection. The angular orientation of the bars is indicated on scale plate 38, as should be apparent from FIG. 6.

FIG. 7 illustrates a further modification of the invention. In FIG. 7, plate-like members 1, 2 and couplings 5, 6 are the same as those shown in FIG. 1. End members 40, 41, connected respectively to couplings 5, 6 are connected to an intermediate elongated member 42 via respective adjustable couplings 43, 4, each coupling having associated scale members 45, 46, respectively. The intermediate member 42 may have scale markings 47, 48 thereon to cooperate with the scale members 45, 46, respectively, to indicate the relative angular orientations of the members 40, 41 to the intermediate member 42. The scale markings 47, 48 may be located on the end members 40, 41, depending upon which member the scale 45, 46 is attached to. For example, if scales 45, 46 are fixedly connected to relative to the end members 40, 41, respectively, then the scale markings 47, 48 are properly located on the intermediate member 42, and vice versa. The couplings 43, 44 and associated scales 45, 46 are the same as coupling 15 and associated scale 21 illustrated in FIGS. 1-3. Other suitable couplings and scales could be used, as should be apparent.

Appropriate orthopedic corrections can be made using the device of the present invention by angularly orienting the various members, via the adjustable couplings, by precise amounts as indicated on the respective scales. The apparatus will maintain its adjustment indefinitely and, adjustments are easily repeatable with a high degree of accuracy. Moreover, the device is simple in construction and inexpensive to manufacture, thereby making it desirable from a commercial point of view.

While the invention has been described above with respect to particular apparatus and embodiments, it should be clear that various modifications and alterations may be made within the scope of the appended claims. Moreover, features of the respective embodiments can be interchanged, as should be apparent to one oridinarily skilled in the art.

I claim:

1. An orthopedic appliance comprising:
    a pair of connection means for connection to a respective shoe of a patient;
    at least three elongated members, each having first and second ends, one of said elongated members comprising a central member and the other two of said elongated members each having ends which are pivotally connected to said central member at the respective opposite ends of said central member, the free ends of each other two elongated members being coupled to a respective connection means;
    adjustment means for adjustably connecting said connection means to the respective free ends of said other two elongated members;
    said elongated members extending between and spanning the distance between said connecting means to maintain the respective connecting means spaced apart;
    said pivotal connections of said elongated members being intermediate said respective connection means;
    means at said respective pivotal connections of said elongated members for releasing and locking said respective pivotal connections to permit pivoting of said other two elongated members relative to said central member, independent of the adjustable connection of said connection means to said respective free ends of said other two elongated members, and for locking of said elongated members relative to each other at a desired relative pivotal angular orientation between said elongated members; and
    scale means at said respective pivotal connections for indicating the angular orientation of each of said other two elongated members relative to said central member about said pivotal connections.

2. The orthopedic appliance according to claim 1 wherein said other two elongated members have substantially equal lengths.

3. The orthopedic appliance according to claim 1 or 2, wherein said central member is substantially longer than said other two elongated members.

4. The orthopedic appliance according to claim 1 wherein said elongated members are substantially flat bar-like members.

5. The orthopedic appliance according to claim 4 wherein said other two elongated members are twisted approximately 90° substantially about their respective longitudinal axis.

6. The orthopedic appliance according to any one of claims 1, 4 or 5, further comprising scale means at each of said adjustment means to indicate the angular orientation of said connection means relative to said elongated members, and therefore of a shoe of a patient, relative to said elongated members.

7. The orthopedic appliance according to claim 6 wherein said adjustment means is adjustable in a plane substantially perpendicular to the plane in which said other two elongated members are pivotally movable relative to said central member.

* * * * *